United States Patent [19]

Lover et al.

[11] 4,146,619
[45] Mar. 27, 1979

[54] SILOXANE TOXICANTS

[75] Inventors: Myron J. Lover, Mountainside; Arnold J. Singer, South Orange; Donald M. Lynch, Waldwick; William E. Rhodes, III, Cranford, all of N.J.

[73] Assignee: Block Drug Company Inc., Jersey City, N.J.

[21] Appl. No.: 802,013

[22] Filed: May 31, 1977

[51] Int. Cl.$^2$ .......................................... A61K 31/695
[52] U.S. Cl. ....................................................... 424/184
[58] Field of Search ........................................ 424/184

[56] References Cited

U.S. PATENT DOCUMENTS

| | | | |
|---|---|---|---|
| 2,681,878 | 6/1954 | Kauppi | 424/184 |
| 2,727,846 | 12/1955 | Talbot | 424/184 |
| 3,470,292 | 9/1969 | Marschner | 424/184 X |
| 3,567,820 | 3/1971 | Sperti | 424/184 X |
| 3,880,996 | 4/1975 | Fisher | 424/184 |
| 3,953,591 | 4/1976 | Snyder | 424/80 |

FOREIGN PATENT DOCUMENTS

| | | | |
|---|---|---|---|
| 503996 | 6/1954 | Canada | 424/184 |
| 829873 | 12/1967 | Canada | 424/184 |

*Primary Examiner*—Allen J. Robinson
*Attorney, Agent, or Firm*—Ostrolenk, Faber, Gerb & Soffen

[57] ABSTRACT

Linear siloxane polymers have been found to exhibit pediculicidal and/or ovicidal activity.

7 Claims, No Drawings

SILOXANE TOXICANTS

BACKGROUND OF THE INVENTION

There are only a relatively few pediculicides which are commercially available today. The most popular pediculicidal toxicants are Lindane (gamma benzene hexachloride), Malathion [(S-1,2-dicarbethoxyethyl)-O,O-dimethyl phosphorodithioate], synergized pyrethrins and Cuprex (a combination of tetrahydronaphthalene, copper oleate and acetone, the acetone not asserted to be active). Because of increased concern about the overall safety of some of the known ectoparasitic toxicants, the search for new, safe and effective pediculicides has intensified recently.

Many species of insects encase their ova in protective sheaths which are impregnable to most toxicants. The "gestation" period of the egg is often relatively long in comparison to the life cycle of the adult forms. Thus, an agent effective only against adults must persist for the lifetime of the developing ovum or must be reapplied as successive hatching occurs.

It has now been found that linear siloxane polymers exhibit pediculicidal and/or ovicidal activity. These compounds are known materials. For example, simethicone is widely used as an antiflatulent.

It is the object of this invention to provide new safe and effective toxicants for lice and their ova. This and other objects of the invention will become apparent to those skilled in the art from the following detailed description.

SUMMARY OF THE INVENTION

This invention relates to ectoparasiticidal toxicants and a method of controlling ectoparasites. More particularly, the invention relates to the use of linear siloxane polymers as toxicants for lice and/or their ova and to toxicant compositions containing such polymers.

DESCRIPTION OF THE PREFERRED EMBODIMENT

The toxicants of this invention are the linear siloxane polymers having a viscosity of less than about 20,000 centistokes, preferably less than about 10,000 centistokes and most preferably about 1,000 centistokes or less. The polymers are characterized by repeating units $R_2SiO$ in which each R is individually alkyl or aryl. In most commercially available polysiloxanes, the R groups are usually methyl or a combination of methyl and phenyl, i.e., dimethicones (CTFA official name for dimethylpolysiloxanes) and phenyldimethicone. The instant toxicants include simethicone which is a mixture of fully methylated linear siloxane polymers containing 93-99% dimethicone units stabilized with trimethylsiloxy [$(CH_3)_3SiO$-] end blocking units and 4-4.5% silicon dioxide. The polysiloxanes used in this invention are relatively inert pharmacologically, are chemically stable and are non-corrosive.

One or more of the toxic polymers of the present invention can be incorporated into an active toxicant composition which can be in the form of a liquid, powder, lotion, cream, gel or aerosol spray, or foam as the result of formulation with inert pharmaceutically acceptable carriers by procedures well known in the art. Any pharmaceutically acceptable carrier, whether aqueous or not aqueous, which is inert to the active ingredient can be employed. By inert is meant that the carrier does not have a substantial detrimental effect on the pediculicidal or ovicidal toxicant activity of the active ingredient.

The active polymers are incorporated into the toxicant composition used to treat the substrate (human or animal) in need of such treatment, believed to be in need of such treatment, or desired to be prophylactically protected in an effective toxicant amount. By such amount is meant the amount which will cause at least 50% of the ectoparasites exposed in the two minute immersion tests described below to die within 24 hours in the case of lice and within 2 weeks in case of the ova. The minimum concentration of polymer required to provide an effective toxic amount varies considerably depending on the particular polymer, the particular inert pharmaceutically acceptable carrier being employed and any other ingredients which are present. Thus, in one case a 10% concentration may suffice, while in other cases, concentrations as high as 25% may be required to obtain an effective toxic dose. Usually, the polymer will be used in concentrations of about 5 to 100% and most preferably at concentrations of about 10 to 100%.

The instant polymers can also be employed as an adjunct toxicant in a preparation which otherwise exhibits pediculicidal and/or ovicidal activity. In such preparations, the term "effective toxic dose" means that amount which will increase the mortality rate by at least about 20% in the standard immersion tests.

The two minute immersion tests referred to above is carried out as follows:

Pediculicidal activity: A 50 ml beaker is filled with tap water and allowed to come to room temperature (about 20° C.). Ten young adult male and ten young adult female lice (*Pediculus humanus corporis*) of the same age group and from the same stock colony are placed on a 2×2 cm coarse mesh path. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute the patch is removed and placed on paper toweling. The lice are then transferred to a 4×4 cm black corduroy cloth patch and this point of time is considered zero hours. Thereafter, the corduroy patch is placed in a petri dish which is covered and stored in a 30° C. holding chamber.

Ovicidal activity: 15 adult, 5 to 10 day old, female lice (*Pediculus humanus corporis*) are placed on a 2×2 cm nylon mesh patch which is placed on a petri dish, covered and maintained in an incubator at 30° C. for 24 hours. The adult lice are then removed and the number of plump, viable eggs and shriveled non-fertile eggs on the patch are recorded. The sample to be tested, maintained at room temperature, is shaken until homogeneous and poured into a 50 ml beaker. Immediately after the pouring, the mesh patch is placed into the beaker, allowed to submerge, and after two minutes is removed and immediately plunged into a 50 ml beaker containing tap water at room temperature (about 24° C.). The patch is vigorously agitated every ten seconds and after one minute, the patch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

In both the pediculicidal and ovicidal two minute immersion tests, controls are run in identical manner to that described with room temperature (24° C.) tap water substituted for the sample to be tested. The results of the tests reported are net results.

The pediculicidal and ovicidal activity of various toxicants of the instant invention were tested in the two minute immersion tests described above. The ratings set forth represent the percent mortality observed. The polymers were evaluated in undiluted form (UD) or in a combination (C) containing 15 (w/w) percent polymer, 25% isopropanol and 60% aqueous carrier.

| Compound | Viscosity in centistokes | % Mortality Pediculicidal UD | C | Ovicidal UD | C |
|---|---|---|---|---|---|
| Phenyldimethicone | 22.5 | 100 | 100 | 94 | 11 |
| Dimethicone | 100 | 100 | 100 | 100 | 72 |
| Dimethicone | 350 | 100 | 100 | 100 | 35 |
| Dimethicone | 900 | 100 | 100 | 100 | 52 |
| Dimethicone | 1,000 | 100 | 100 | 100 | 38 |
| Dimethicone | 12,000 | 100 | 100 | 100 | 0 |

The pediculicidal activity of various polysiloxanes as a function of concentration in 25% isopropanol, 7% Polysorbate 80 emulsifier, and water Q.S. was studied and the results are shown below.

| Phenyldimethicone 22.5 centistokes % W/W | % Mortality |
|---|---|
| 15 | 100 |
| 13 | 100 |
| 11 | 95 |
| 9 | 80 |
| 7 | 75 |
| 5 | 0 |
| 3 | 0 |
| 1 | 0 |

| Dimethicone, 100 centistokes % W/W | % Mortality |
|---|---|
| 15 | 100 |
| 13 | 95 |
| 11 | 95 |
| 9 | 100 |
| 7 | 90 |
| 5 | 10 |
| 3 | 5 |
| 1 | 5 |

| Dimethicone, 350 centistokes % W/W | % Mortality |
|---|---|
| 15 | 100 |
| 13 | 100 |
| 11 | 100 |
| 9 | 100 |
| 7 | 95 |
| 5 | 85 |
| 3 | 25 |
| 1 | 0 |

| Dimethicone, 900 centistokes % W/W | % Mortality |
|---|---|
| 15 | 100 |
| 13 | 100 |
| 11 | 100 |
| 9 | 85 |
| 7 | 70 |
| 5 | 20 |
| 3 | 20 |
| 1 | 0 |

| Dimethicone, 1000 centistokes % W/W | % Mortality |
|---|---|
| 15 | 100 |
| 13 | 100 |
| 11 | 95 |
| 9 | 85 |
| 7 | 90 |
| 5 | 65 |
| 3 | 40 |
| 1 | 0 |

| Dimethicone, 12,000 centistokes % W/W | % Mortality |
|---|---|
| 15 | 100 |
| 13 | 85 |
| 11 | 40 |
| 9 | 10 |
| 7 | 75 |
| 5 | 0 |
| 3 | 0 |
| 1 | 0 |

As can be seen from the foregoing, the viscosity range of 100–1000 centistokes for the dimethicones tested exhibit the highest pediculicidal activity below a 15% W/W concentration. The one phenyldimethicone derivative tested displays equivalent activity but at a much lower viscosity value.

As noted above, various end use formulations can be prepared. Some typical formulations are set forth below and the amounts recited are percentages by weight.

EXAMPLES

| Gel | |
|---|---|
| Isopropanol | 25.0 |
| Dimethicone, 100 centistokes | 15.0 |
| Sorbitan monolaurate | 7.5 |
| Carbomer 940 | 3.0 |
| Triethanolamine | 4.0 |
| Water | 45.5 |
| Aerosol Spray | |
| Ethanol | 70.0 |
| Phenyldimethicone, 22.5 centistokes | 15.0 |
| Isobutane | 15.0 |
| Powder | |
| Talc | 90.0 |
| Dimethicone, 900 centistokes | 10.0 |
| Quick breaking aerosol foam | |
| Mono and diglycerides from the glycerides of edible fats | 8.0 |
| Isopropanol | 25.0 |
| Dimethicone, 350 centistokes | 15.0 |
| Glycerine | 3.0 |
| Water | 41.0 |
| Isobutane | 8.0 |
| Stick | |
| Sodium stearate | 8.0 |
| Ethanol | 77.0 |
| Phenyldimethicone, 22.5 centistokes | 15.0 |
| Cream | |
| Beeswax | 10.0 |
| Dimethicone, 100 centistokes | 15.0 |
| Cetyl alcohol | 3.0 |
| Mineral oil | 8.0 |
| Glycerylmonostearate | 5.0 |
| Sorbitan monolaurate | 4.0 |
| Isopropanol | 25.0 |
| Xanthan gum | 0.2 |
| Sodium borate, pentahydrate | 0.75 |
| Water | 29.05 |

Various changes and modifications can be made in the present invention without departing from the scope and the spirit thereof. The various embodiments which have been described above were set forth for illustration purposes only and were not intended to limit the invention. Unless otherwise specified, throughout this specification and claims, all temperatures have been in degrees Centigrade and all parts and percentages by weight.

We claim:

1. A method of controlling ectoparasites or their ova which comprises applying to an animal or human in need of such control, an effective toxic amount of at least one linear siloxane polymer having repeating units $R_2SiO$ in which each R is individually alkyl or aryl and having a viscosity of less than about 20,000 centistokes.

2. The method of claim 1 wherein said polymer has a viscosity of less than about 10,000 centistokes.

3. The method of claim 2 wherein said polymer has a viscosity of about 1,000 centistokes or less.

4. The method of claim 1 wherein said polymer is dimethicone or phenyldimethicone.

5. The method of claim 1 wherein said polymer is simethicone.

6. The method of claim 1 wherein said polymer is employed in combination with an inert pharmaceutically acceptable carrier.

7. The method of claim 6 wherein said carrier is aqueous.